United States Patent
Cauvin et al.

(10) Patent No.: US 9,156,954 B2
(45) Date of Patent: Oct. 13, 2015

(54) EMULSION POLYMERISATION METHOD

(75) Inventors: Severine Cauvin, Mons (BE); Sophie Hanssens, Chastre (BE); Alberto Petrosino, Manage (BE); Benoit Rassart, La Louviere (BE); Blondine Van Roy, Wezembeek-Oppem (BE)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/002,789

(22) PCT Filed: Mar. 1, 2012

(86) PCT No.: PCT/EP2012/053520
§ 371 (c)(1),
(2), (4) Date: Sep. 3, 2013

(87) PCT Pub. No.: WO2012/119916
PCT Pub. Date: Sep. 13, 2012

(65) Prior Publication Data
US 2014/0093547 A1 Apr. 3, 2014

(30) Foreign Application Priority Data

Mar. 4, 2011 (GB) .................................. 1103690.2

(51) Int. Cl.
| | | |
|---|---|---|
| C08J 3/05 | (2006.01) |
| A61K 8/06 | (2006.01) |
| A61K 8/891 | (2006.01) |
| A61Q 5/02 | (2006.01) |
| A61Q 5/12 | (2006.01) |
| A61Q 19/00 | (2006.01) |
| C08J 3/03 | (2006.01) |
| C08L 83/04 | (2006.01) |
| A61Q 19/10 | (2006.01) |
| C11D 17/00 | (2006.01) |
| C08G 77/16 | (2006.01) |

(52) U.S. Cl.
CPC ... C08J 3/05 (2013.01); A61K 8/06 (2013.01); A61K 8/062 (2013.01); A61K 8/891 (2013.01); A61Q 5/02 (2013.01); A61Q 5/12 (2013.01); A61Q 19/00 (2013.01); A61Q 19/10 (2013.01); C08J 3/03 (2013.01); C08L 83/04 (2013.01); C11D 17/0021 (2013.01); A61K 2800/21 (2013.01); C08G 77/16 (2013.01); C08J 2383/04 (2013.01)

(58) Field of Classification Search
None
See application file for complete search history.

(56) References Cited

U.S. PATENT DOCUMENTS

| | | | |
|---|---|---|---|
| 4,990,555 A | 2/1991 | Trego | |
| 5,504,150 A * | 4/1996 | Gilson et al. | 524/837 |
| 6,232,396 B1 | 5/2001 | Dong et al. | |
| 6,235,834 B1 | 5/2001 | Gee et al. | |
| 7,683,119 B2 * | 3/2010 | Creutz et al. | 524/588 |
| 8,007,775 B2 | 8/2011 | Hossainy et al. | |
| 8,211,973 B2 | 7/2012 | Creutz et al. | |
| 8,575,266 B2 | 11/2013 | Brehm et al. | |
| 8,580,862 B2 * | 11/2013 | Barnes et al. | 516/55 |
| 2001/0012872 A1 | 8/2001 | Dong et al. | |
| 2002/0165505 A1 * | 11/2002 | Gee et al. | 604/289 |
| 2006/0111452 A1 * | 5/2006 | Wallace et al. | 516/53 |
| 2007/0244213 A1 * | 10/2007 | Wallace | 523/102 |
| 2008/0033062 A1 * | 2/2008 | Herzig et al. | 516/55 |
| 2010/0204398 A1 | 8/2010 | Creutz et al. | |
| 2012/0171147 A1 * | 7/2012 | Rautschek | 424/70.12 |
| 2013/0116381 A1 * | 5/2013 | Keinath et al. | 524/860 |

FOREIGN PATENT DOCUMENTS

| | | | |
|---|---|---|---|
| EP | 0739929 A2 | 10/1996 |
| EP | 0748832 A2 | 12/1996 |
| EP | 1069149 A1 | 1/2001 |
| EP | 1072629 A2 | 1/2001 |
| EP | 1352011 | 1/2006 |
| EP | 1846478 B1 | 12/2008 |
| JP | 11-071522 A | 3/1999 |
| JP | 2000-053769 A | 2/2000 |
| JP | 2007-297533 A | 11/2007 |
| JP | 2012201867 | 10/2012 |
| WO | WO 02/42360 A2 | 5/2002 |
| WO | WO 2004069899 A1 | 8/2004 |
| WO | WO 2005040250 A1 | 5/2005 |
| WO | 2006073631 | 7/2006 |
| WO | WO 2009129175 A1 | 10/2009 |
| WO | WO 2011032824 A1 | 3/2011 |

OTHER PUBLICATIONS

English language abstract and translation for JP 11-071522 extracted from PAJ database on Mar. 10, 2014, 43 pages. English language abstract and translation for JP 2000-053769 extracted from PAJ database on Mar. 10, 2014, 43 pages.

(Continued)

*Primary Examiner* — Robert S Loewe
(74) *Attorney, Agent, or Firm* — Baltazar Gomez

(57) ABSTRACT

The invention relates to a method for the production of silicone in water emulsions by emulsion polymerization. The emulsion contains particles of an organopolysiloxane polymer having an average particle diameter of less than 1 μm. The method comprises: —combining a silanol end-blocked organosiloxane starting polymer, water, and a surfactant; said starting polymer having a viscosity of at least 2 Pa·s preferably at least 2.5 Pa·s preferably at least 3.5 Pa·s preferably at least 4 Pa·s and up to 150 Pa·s; —emulsifying the starting polymer by agitating or shearing the ingredients; —polymerizing the starting polymer to form a longer chain silanol end-blocked organopolysiloxane polymer; wherein at least a portion of said polymerizing step is performed at a temperature of less than or equal to 16° C. preferably less than or equal to 15° C.

21 Claims, No Drawings

(56) References Cited

OTHER PUBLICATIONS

English language abstract and translation for JP 2007-297533 extracted from PAJ database on Mar. 10, 2014, 44 pages.

English language abstract for WO 2011/032824 extracted from espacenet.com database on Mar. 10, 2014, 45 pages.
International Search Report for PCT/EP2012/053520 dated Apr. 12, 2012, 3 pages.

* cited by examiner

EMULSION POLYMERISATION METHOD

RELATED APPLICATIONS

This application is the National Stage of International Patent Application No. PCT/EP2012/053520, filed on Mar. 1, 2012, which claims priority to and all the advantages of Great Britain Patent Application No. GB1103690.2, filed on Mar. 4, 2011, the content of which is incorporated herein by reference.

This invention relates to a method for the production of silicone in water emulsions by emulsion polymerisation.

Silicone in water emulsions can be classically prepared by mechanical emulsification of the silicone or by emulsion polymerization. Generally, mechanical emulsification is used when a relatively low viscosity silicone needs to be emulsified. Indeed, above certain viscosities (600 Pa·s), the silicone cannot be emulsified anymore with conventional mixers without the particle size becoming too high.

Thus in order to prepare emulsion of high viscosity silicone, a polymerization reaction is necessary.

Various cyclosiloxanes including octamethylcyclotetrasiloxane (D4) and decamethylcyclopentasiloxane (D5) are extensively used as monomers as they are cost effective and available in large quantities. However, the ring-opening polymerization of cyclosiloxanes is not complete and sometimes a large amount of residual octamethylcyclotetrasiloxane (D4) and decamethylcyclopentasiloxane (D5) stays in the final product (typically 2-10%). Short hydroxyl terminated (poly) diorganosiloxane are also used as starting material using a condensation reaction that leads to silicone emulsions with high internal phase viscosity. In this last method, around 1% octamethylcyclotetrasiloxane (D4) and decamethylcyclopentasiloxane (D5) are generated as an unintended by-product of the condensation reaction. Reducing the presence of solvents, un-reacted siloxanes, catalyst residues, cyclic polymerization by-products, and other impurities in silicone emulsions is an ongoing challenge in the art. The need to reduce such impurities may arise, among other reasons, when such impurities are incompatible with downstream applications (for example, medical, cosmetic, and personal care applications), where the presence of such impurities would reduce the stability of an emulsion, or where regulatory requirements require removal or reduction of their presence. In particular, there is an interest to reduce the presence of cyclosiloxanes, such as octamethylcyclotetrasiloxanes (D4) and decamethylcyclopentasiloxanes (D5), and optionally dodecamethylcyclohexasiloxane (D6), in silicone emulsions.

The abstract of JP11071522A describes a reaction using short hydroxyl-PDMS but the level of cyclics is rather high, being up to 3.5 wt %. U.S. Pat. No. 6,235,834B1 describes an emulsion polymerisation but with the use of various specific anionic surfactants and particle sizes must be above 1 micron which is not appropriate for many applications as it limits the stability of the emulsions.

U.S. Pat. No. 6,232,396B1 describes the process for the preparation of emulsions and shows some control over the condensation reaction to limit the formation of cyclics below 1% but the inventors of the present invention prefer further control over cyclic formation.

WO2009/129175 describes a process for preparing an emulsion composition by forming a mixture of a silanol functional polyorganosiloxane, a boron compound, an emulsifier, and then admixing water to the mixture to form an emulsion. The mixing step is generally conducted at ambient temperature and pressure.

WO2005/040250 describes an emulsion composition containing (i) a linear hydroxyl terminated polydiorganosiloxane, (ii) a silicone MQ resin and (iii) an organofunctional polysiloxane.

EP1069149 describes a method for preparing an emulsion containing particles of an organopolysiloxane polymer with average particle diameter of at least one micron.

The abstract of JP2000053769 describes a polyorganosiloxane emulsion obtained with starting from a silanol group-terminated polydiorganosiloxane having a viscosity of 10 to 3,000 cSt. Density of polydiorganosiloxane being about 1, the viscosity is up to 3 Pa s. The temperature condition of the polymerization is preferably the freezing point of the emulsion to 20° C.

The abstract of JP2007297533 describes a method for producing a functional group-containing diorganopolysiloxane emulsion having a small median diameter, starting from a terminal hydroxydiorganopolysiloxane represented by general formula $H[O-Si(R)_{2n}-OH]_n-OH$ wherein R is a monovalent hydrocarbon group and n is an integer between 10 and 200.

EP1072629 describes a process for making a silicone emulsion comprising preparing a neutral aqueous surfactant by adding to water an anionic surfactant and a base and mixing to form a uniform neutral aqueous surfactant having a pH of about 7. The starting polysiloxane used has a viscosity from about 15 to about 1000 centistokes.

Thus the prior art does not describe a method which can be used to achieve a low rate of cyclic formation for such an emulsion polymerisation reaction, especially with an acceptable average particle size and acceptable polymerization time. An object of the present invention is to mitigate or alleviate at least one of the problems associated with the prior art.

According to a first aspect of the invention, there is provided a method of preparing an emulsion containing particles of an organopolysiloxane polymer having an average particle diameter of less than 1 μm, the method comprising:
(i) combining a silanol endblocked organosiloxane starting polymer, water, and a surfactant; said starting polymer having a viscosity of at least 2 Pa·s, preferably at least 2.5 Pa·s preferably at least 3.5 Pa·s and up to 150 Pa·s
(ii) emulsifying the starting polymer by agitating or shearing the ingredients;
(ii) polymerizing the starting polymer to form a longer chain silanol end-blocked organopolysiloxane polymer;
wherein at least a portion of said polymerising step is performed at a temperature of less than or equal to 16° C., preferably less than or equal to 15° C., preferably less than 14° C.

For certain embodiments the viscosity may be up to 100 Pa·s which assists in producing particle sizes of less than 1 micron.

In certain embodiments the polymerisation step is started at a first temperature and then reduced to a lower temperature, said lower temperature being less than or equal to 15° C., optionally less than 12° C.

Normally the starting temperature is less than or equal to 25° C., optionally less than or equal to 22° C. Normally the starting temperature is more than or equal to 18° C. Thus normally the polymerisation is started at a temperature of above or equal to 18° C., optionally above or equal to 20° C., and reduced to said lower temperature of below or equal to 15° C. For certain embodiments, the lower temperature may be below or equal to 12° C.

For certain embodiments, the portion of the polymerisation step performed at less than or equal to 15° C. is also performed at a temperature more than 2° C., optionally more than 5° C. optionally more than 10° C.

Viscosities are expressed in Pascal-seconds (Pa·s) and are typically measured following ASTM D4287 using a Brookfield type of viscosimeter namely a cone/plate CP-52 at 25° C. at 1 rpm for the starting organopolysiloxane and at 25° C. for final organopolysiloxane with a cone/plate DVIII NO. 52 at 0.3 rpm.

Thus the inventors of the present invention have gone against the teaching in the art and increased the viscosity of the starting polymer to at least 2, preferably at least 2.5 preferably at least 3.5 preferably 4 Pa·s which, in itself, will increase the particle size. This is in marked contrast to the accepted wisdom in the art where particle size is minimised to maintain a stable emulsion. Indeed the use of polymerisation emulsion in preference to mechanical emulsion is intended to minimise particle size and so including a step which would result, in itself, in an increased particle size is not expected. Moreover one may expect such a high viscosity starting polymers to be extremely difficult to emulsify before the polymerisation reaction.

Nevertheless to mitigate or eliminate the increase in particle size it is preferred to use a high shear method, that is the siloxane starting polymer, the surfactant and the water are fed into a high shear mixer through a single supply line and the pressure in the supply line at the inlet to the high shear mixer is monitored to be within 20% of a target pressure predetermined to give a desired emulsion particle size. The target pressure may be within the range 0.05 to 40 bar.

Typically a high-shear dynamic mixer (Homomic line mixer from Tokushu Kika Kogyo Co. or Greerco® From Chemineer, Inc.) is used and a method followed as described in EP1352011, the disclosure of which is incorporated herein in its entirety by reference.

Alternatively to a high-shear dynamic mixer, a high-shear device like a Change Can Mixer (Charles Ross & Son Company) can be used. The emulsion is thus supplied as a concentrated emulsion which is then diluted and reacted in a tank or a reactor.

Thus an advantage of certain embodiments is that the particle sizes are kept reasonably small, normally less than 1 µm preferably less than 0.8 µm sometimes less than 0.6 µm or less than 0.5 µm. This provides a more stable emulsion. Typically, Dv[0.5] is below 0.5 µm. The advantage of having small particle size is that reaction time is reduced and it improves the stability of the emulsion upon creaming.

Average particle diameter sizes are measured using a Malvern Mastersizer 2000 or with a Microtrac UPA150. Dv[0.5] is the volume average diameter, [0.5] means that 50% of the volume of the sample has a particle diameter below this value.

The inventors of the present invention discovered that managing the temperature profile by performing at least a portion of the polymerisation at or below 16° C. preferably at or below 15° C. more preferably at or below 14° C. surprisingly results in a reduced cyclics level, without a significant effect on the reaction time.

In certain embodiments starting the reaction at least 18° C. and at most 25° C.; and then decreasing to 15° C. or below is particularly beneficial since the reaction time can be reduced by at least 1 hour compared to working at a constant temperature at or below 15° C.

The reaction can be completed in, for example, 1-24 hours, preferably 2 to 16 hours for example 2-10 hours, optionally 2-8 hours. However, if less acid/surfactant catalyst is added then the reaction can take longer to complete up to 24 hours. Moreover during large scale production of preferred embodiments, the polymerisation may be started without waiting for the emulsion to be cooled to below 15° C. A benefit of this is that it can save production time, potentially as much as four hours or more.

Moreover in large scale production less energy is required since the starting polymer of certain embodiments does not need to be cooled to below 15° C. before starting the polymerisation.

The time at said lower temperature may be at least 30%, optionally more than 60% of the total reaction time. The lower temperature is normally more than 2° C., typically more than 5° C. preferably more than 10° C.

Typically the process is a continuous process and so the starting silanol endblocked organosiloxane polymer, surfactant(s) and water are continuously fed to the high shear mixer in such proportions so as to form a viscous oil in water emulsion which is typically continuously withdrawn from the mixer.

The surfactant is normally anionic such as alkylaryl sulfonic acids and their salts, alkyl sulfonic acids and their salts, alkylesters of sulfosuccinic acids and their salts, alkyl aryl polyethylene glycol ether sulfates, alkyl polyethylene glycol ether sulphates, alkyl ether of sulfuric acids and their salts which have some catalytic activity for condensation polymerisation of polysiloxanes naturally or in acidic media. However, the anionic surfactant is more preferably introduced for the emulsification under its neutralized form, for example alkylarylsulfonic and alkylsulfonics acids are normally neutralized by a base, such as triethanolamine (TEA) or sodium hydroxide, and the product of the neutralisation is used for the emulsification. The salts forms of sulphonates and sulphates, such as sodium alkylbenzene sulphonate, can also be used directly if they do not present any catalytic activity for condensation polymerization of polysiloxane.

Example of suitable (but not exhaustive) surfactants are hexylbenzene sulfonic acid, octylbenzene sulfonic acid, decylbenzene sulfonic acid, linear or branched dodecylbenzene sulfonic acid, linear or branched C10-C14 benzene sulfonic acid, sodium linear or branched C10-C14 benzene sulfonate, ammonium linear or branched C10-C14 benzene sulfonate, linear or branched C10-C14 sulphates, sodium lauryl sulphates, sodium laureth sulphates and the mixture of the above mentioned Typically step (iii) is performed by adding a condensation specific acid catalyst. This can be further addition of catalytically active anionic surfactant, typically under their acidic form, as described above or any suitable strong acid. One particularly suitable acid is a mixture of alkylbenzene sulfonic acids, alkylsulfonic acids, sulfuric acid or hydrochloric acid.

The amount of water used for preparing the emulsion being 10-90 percent by weight based on the total weight of the emulsion.

Typically the amount of starting silanol end-blocked organopolysiloxane used for preparing the emulsion being 25-80 wt %, optionally 35-65 wt %, based on the total weight of the emulsion.

The amount of anionic surfactant used for preparing the emulsion being 0.5-10 wt %, optionally 1.5-8 wt %, based on the total weight of the emulsion.

In case of the use of a catalytically active anionic surfactant, the molar ratio between the catalytically active anionic surfactant and the base to neutralise it is normally 1-1.5.

A molar ratio of active acid $R^+$ is defined as being the ratio between the molar amount of catalytically active anionic surfactant plus the molar amount of condensation catalyst minus the molar amount of base divided by the molar amount of catalytically active anionic surfactant.

The amount of condensation catalyst is calculated such as R$^+$ may be between 0.1 and 5, optionally 0.9 and 1.5.

Typically the polymerising step (iii) is continued until the resulting organopolysiloxane polymer has attained the desired increase in viscosity. Neutralizing agent is normally added to stop the polymerisation to reach a final pH, which may be in the range of 6.5-8, most typically between 7-7.5.

Suitable neutralizing agents are strong or weak bases such as amines, typically triethanolamine or a hydroxide salt, such as sodium hydroxide.

The viscosity of the starting polymer may be above 2 Pa·s, preferably above 3.5 more preferably above 4 Pa s.

The silanol end-blocked siloxane starting polymer may have a formula:

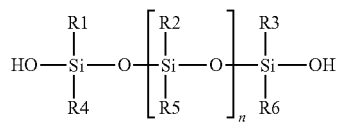

wherein $R_1$ to $R_6$ represent an alkyl group containing 1-6 carbon atoms or an aryl group, and n is normally in the range of 300-2000, preferably 500-2000 and more normally in the range of 500-1000.

After step (ii) and before step (iii), the concentrated oil in water emulsion containing the siloxane starting polymer may be diluted further, for example by the addition of water especially when a continuous process is used.

Typically, internal phase viscosity, that is the viscosity of the polymerised particles, is 600 Pa·s to 5000 Pa·s for certain embodiments of the present invention.

An advantage of certain embodiments is that the reaction is controlled and so the level of D4, D5 and D6 formed during the reaction attained to be less than 0.1% for one or more, sometimes each of D4, D5 and D6.

The emulsifying step may be continued until the particle size Dv0.5 may be below 1 μm optionally below 0.5 μm.

For certain embodiments of the invention, the emulsion can contain some additives such as non-ionic surfactant(s) used to reduce particle size during the emulsification or added in post-addition for the stability of the emulsion, biocides for preventing microbiological growth, and/or organic or inorganic thickener for improving emulsion stability towards creaming. In some preferred embodiments, the surfactant is an anionic surfactant with optionally one or more non-ionic surfactant(s). It can be used in a weight percentage of maximum 3% preferably below 1% in percentages of the weight of the emulsion containing the silanol end-blocked organosiloxane, water and surfactant.

Examples of non-ionic surfactants include polyoxyalkylene alkyl ethers such as polyethylene glycol long chain (9-22C, especially 12-14C) alkyl ether, polyoxyalkylene sorbitan ethers, polyoxyalkylene alkoxylate esters, ethylene oxide propylene oxide copolymers, polyvinyl alcohol, glyceride esters and alkylpolysaccharides.

The polymerisation step is normally stopped before 0.1% of each of D4 and D5 are formed.

The invention provides a composition comprising an emulsion containing particles of a silanol end-blocked organopolysiloxane polymer having an average particle diameter of less than 1 μm, the composition containing less than 0.1 wt % of octamethylcyclotetrasiloxane (D4) and less than 0.1 wt % decamethylcyclopentasiloxane (D5).

The composition is suitable for use within a hair shampoo, hair conditioner, hair treatment, for skin care products, for paper or textile treatment, leather treatment and/or home care applications.

Embodiments of the invention will now be described by way of example only.

COMPARATIVE EXAMPLE

First, to provide a composition comprising an acid, a base and the starting end-blocked siloxane polymer, 116.8 g of Marlon AS 3 (alkylbenzene sulfonic acid) was added to 1572.6 g of water in a 5 L plastic pail under stirring (250 rpm). 99 g of triethanolamine LFG 85% was then added to the surfactant solution. When the aqueous solution was homogeneous, 2200 g of a Me$_2$SiOH terminated dimethylpolysiloxane having a viscosity of approximately 100 mPa sec and a number average molecular weight of approximately 4,000 was then added under stirring (500 rpm). After 1 hour stirring, a coarse emulsion was obtained and then passed three times in a Rannie mixer at 700 bar. This masterbatch emulsion had average mean particle size of 0.169 micron.

732 g of this masterbatch emulsion was poured in a 1 liter double-wall glass reactor. The temperature was decreased until 21° C. and, in order to start the emulsion polymerisation reaction, 55.06 g of sulfuric acid 10% was added under stirring (500 rpm) for 5 minutes. After 5 minutes, the stirring rate was decreased to 250 rpm. The temperature of the reaction was decreased slowly down to 10° C. in 10 hours. After 10 hours, the reaction was stopped by the addition of 21.5 g of triethanolamine. The viscosity of the final endblocked siloxane was 1600 Pa·s. The level of D4, D5 and D6 formed are respectively 0.225, 0.046 and 0.031 wt %. In this comparative example the level of D4 was too high to get the desired polysiloxane viscosity (1000 Pa s) for the application.

Example 1

First, to provide a composition comprising an acid, base and the starting polymer, 400 g of triethanolamine was added into Change Can Mixer followed by the addition of 400 g of Marlon AS 3 (alkylbenzene sulfonic acid). The mixture was gently mixed with a scrapper at 30 rpm. 150 g of distilled water was then added under stirring (60 rpm). 4400 g of a Me$_2$SiOH terminated dimethylpolysiloxane having a viscosity of approximately 50,000 mPa sec. (cP) and a number average molecular weight of approximately 64,000 was then added. The mixture was stirred for 20 minutes at 3500 rpm. A concentrated oil in water emulsion was obtained. 2548 g of dilution water was then slowly poured. This masterbatch emulsion had average mean particle size of 0.233 micron.

545 g of this masterbatch emulsion was further diluted with 202 g of water in a 1 liter double-wall glass reactor. The temperature was decreased until 21° C. and, in order to start the emulsion polymerisation reaction, 92.8 g of sulphuric acid 10% was added under stirring (500 rpm) for 5 minutes. After 5 minutes, the stirring rate was decreased to 250 rpm. The temperature of the reaction was decreased slowly down to 14° C. in 2 hours and down to 10° C. in 4 hours. After 6 hours, the reaction was stopped by the addition of 35 g of triethanolamine. The polymer extracted from the emulsion had a viscosity of 2600 Pa·s. The level of D4, D5 and D6 formed are respectively 0.068, 0.011 and 0 wt %.

Example 2

First, to provide a composition comprising an acid, base and the starting polymer, 402 g of triethanolamine was added into Change Can Mixer followed by the addition of 464 g of Marlon AS 3 (alkylbenzene sulfonic acid). The mixture was gently mixed with a scrapper at 30 rpm. 150 g of distilled water was then added under stirring (60 rpm). 4400 g of a Me$_2$SiOH terminated dimethylpolysiloxane having a viscosity of approximately 14,000 mPa sec. (cP) and a number average molecular weight of approximately 44,000 was then added. The mixture was stirred for 20 minutes at 3500 rpm. A concentrated oil in water emulsion was obtained. 2550 g of dilution water was then slowly poured. This masterbatch emulsion had average mean particle size of 0.196 micron.

652 g of this masterbatch emulsion was further diluted with 101.2 g of water in a 1 liter double-wall glass reactor. The temperature was decreased until 21° C. and, in order to start the emulsion polymerisation reaction, 99.8 g of sulfuric acid 10% was added under stirring (500 rpm) for 5 minutes. After 5 minutes, the stirring rate was decreased to 250 rpm. The temperature of the reaction was decreased slowly down to 10° C. in 4 hours. After 6 hours, the reaction was stopped by the addition of 37.7 g of triethanolamine. The polymer extracted from the emulsion had a viscosity of 2750 Pa·s. The level of D4, D5 and D6 formed are respectively 0.072, 0.012 and 0 wt %.

Example 3

First, to provide a composition comprising an acid, base and the starting polymer, 400 g of triethanolamine was added into Change Can Mixer followed by the addition of 464 g of Marlon AS 3 (alkylbenzene sulfonic acid). The mixture was gently mixed with a scrapper at 30 rpm. 150 g of distilled water was then added under stirring (60 rpm). 4400 g of a Me$_2$SiOH terminated dimethylpolysiloxane having a viscosity of approximately 5,000 mPa sec. (cP) and a number average molecular weight of approximately 33,000 was then added. The mixture was stirred for 35 minutes at 3500 rpm. A concentrated oil in water emulsion was obtained. 2550 g of dilution water was then slowly poured. This masterbatch emulsion had average mean particle size of 0.200 micron.

700.1 g of this masterbatch emulsion was further diluted with 100.2 g of water in a 1 liter double-wall glass reactor. The temperature was decreased until 21° C. and, in order to start the emulsion polymerisation reaction, 97.6 g of sulfuric acid 10% was added under stirring (500 rpm) for 5 minutes. After 5 minutes, the stirring rate was decreased to 250 rpm. The temperature of the reaction was decreased slowly down to 10° C. in 4 hours. After 6 hours, the reaction was stopped by the addition of 36.3 g of triethanolamine. The polymer extracted from the emulsion had a viscosity of 1300 Pa·s. The level of D4, D5 and D6 formed are respectively 0.083, 0.016 and 0.006 wt %.

Example 4

First, to provide a composition comprising an acid, base and the starting polymer, 198 g of triethanolamine was added into Change Can Mixer followed by the addition of 234 g of Marlon AS 3 (alkylbenzene sulfonic acid). The mixture was gently mixed with a scrapper at 30 rpm. 176 g of distilled water was then added under stirring (60 rpm). 4400 g of a Me$_2$SiOH terminated dimethylpolysiloxane having a viscosity of approximately 5,000 mPa sec. (cP) and a number average molecular weight of approximately 33,000 was then added. The mixture was stirred for 25 minutes at 3500 rpm. A concentrated oil in water emulsion was obtained. 2922 g of dilution water was then slowly poured. This masterbatch emulsion had average mean particle size of 0.297 micron.

821.3 g of this masterbatch emulsion was poured in a 1 liter double-wall glass reactor. The temperature was decreased until 21° C. and, in order to start the emulsion polymerisation reaction, 62.09 g of sulphuric acid 10% was added under stirring (500 rpm) for 5 minutes. After 5 minutes, the stirring rate was decreased to 250 rpm. The temperature of the reaction was decreased slowly down to 10° C. in 4 hours. After 10 hours, the reaction was stopped by the addition of 24.5 g of triethanolamine. The polymer extracted from the emulsion had a viscosity of 1500 Pa·s. The level of D4, D5 and D6 formed are respectively 0.087, 0.017 and 0.008 wt %.

Example 5

First, to provide a composition comprising an acid, base and the starting polymer, 400 g of triethanolamine was added into Change Can Mixer followed by the addition of 464 g of Marlon AS 3 (alkylbenzene sulfonic acid). The mixture was gently mixed with a scrapper at 30 rpm. 180 g of distilled water was then added under stirring (60 rpm). 4400 g of a Me$_2$SiOH terminated dimethylpolysiloxane having a viscosity of approximately 2,500 mPa sec. (cP). The mixture was stirred for 25 minutes at 3500 rpm. A concentrated oil in water emulsion was obtained. 2521 g of dilution water was then slowly poured. This masterbatch emulsion had average mean particle size of 0.186 micron.

650.1 g of this masterbatch emulsion was poured in a 1 liter double-wall glass reactor. The temperature was decreased until 21° C. and, in order to start the emulsion polymerisation reaction, 99.04 g of sulphuric acid 10% was added under stirring (500 rpm) for minutes. After 5 minutes, the stirring rate was decreased to 250 rpm. The temperature of the reaction was decreased slowly down to 10° C. in 4 hours. After 10 hours, the reaction was stopped by the addition of 25.99 g of triethanolamine TEA. The polymer extracted from the emulsion had a viscosity of 1700 Pa·s. The level of D4, D5 and D6 formed are respectively 0.088, 0.017 and 0.008 wt %.

| | Starting temp. (° C.) | End temp. (° C.) | Starting Viscosity (mPa · s) | Marlon AS 3 (wt %) | TEA (wt %) | R+ | Reaction Time (h) | Final Viscosity (Pa · s) | D4 formation (wt %) | D5 formation (wt %) |
|---|---|---|---|---|---|---|---|---|---|---|
| Example 6a | 21 | 10 | 80000 | 2.9 | 2.5 | 1.14 | 5.0 | 972 | 0.030 | 0.000 |
| Example 6b | 21 | 10 | 80000 | 2.9 | 2.5 | 0.11 | 19.0 | 940 | 0.040 | 0.009 |
| Example 6c | 21 | 10 | 80000 | 2.9 | 2.5 | 4.00 | 3.1 | 902 | 0.050 | 0.009 |
| Example 7a | 10 | 10 | 60000 | 2.9 | 2.5 | 1.14 | 5.0 | 690 | 0.017 | 0.002 |
| Example 7b | 20 | 10 | 60000 | 2.9 | 2.5 | 1.14 | 5.4 | 964 | 0.054 | 0.009 |
| Example 8a | 10 | 10 | 5000 | 2.4 | 2 | 1.14 | 7.5 | 1030 | 0.055 | 0.012 |
| Example 8b | 21 | 10 | 5000 | 2.4 | 2 | 1.14 | 7.5 | 1410 | 0.070 | 0.016 |
| Example 9 | 18 | 15 | 5000 | 2.4 | 2 | 1.14 | 7.5 | 1643 | 0.088 | 0.025 |
| Example 10 | 10 | 10 | 60000 | 2.9 | 2.5 | 1.14 | 10 | 1112 | 0.055 | 0.035 |
| Example 11 | 21 | 10 | 20000 | 2.3 | 2.1 | 1.14 | 3.0 | 710 | 0.067 | 0.023 |

Summary table: level of starting polymer is set at 45 wt % silicone for all the examples described in the table

Masterbatch for Example 6

First, to provide a composition comprising an acid, base and the starting polymer, 313 g of triethanolamine was added into Change Can Mixer followed by the addition of 369 g of Marlon AS 3 (alkylbenzene sulfonic acid). The mixture was gently mixed with a scrapper at 30 rpm. 251 g of distilled water was then added under stirring (60 rpm). 5700 g of a Me$_2$SiOH terminated dimethylpolysiloxane having a viscosity of approximately 80,000 mPa sec. (cP). The mixture was stirred for 25 minutes at 3500 rpm. A concentrated oil in water emulsion was obtained. 1368 g of dilution water was then slowly poured. This masterbatch emulsion had average mean particle size of 0.396 micron.

Masterbatch for Example 7

Same as for example 6 except that the terminated dimethylpolysiloxane has a viscosity of approximately 60,000 mPa sec. (cP). This masterbatch emulsion had average mean particle size of 0.41 micron.

Masterbatch for Example 8 and 9

First, to provide a composition comprising an acid, base and the starting polymer, 259 g of triethanolamine was added into Change Can Mixer followed by the addition of 305 g of Marlon AS 3 (alkylbenzene sulfonic acid). The mixture was gently mixed with a scrapper at 30 rpm. 270 g of distilled water was then added under stirring (60 rpm). 5779 g of a Me$_2$SiOH terminated dimethylpolysiloxane having a viscosity of approximately 5,000 mPa sec. (cP). The mixture was stirred for 25 minutes at 3500 rpm. A concentrated oil in water emulsion was obtained. 1387 g of dilution water was then slowly poured. This masterbatch emulsion had average mean particle size of 0.303 micron.

Masterbatch of Example 10

Same as for example 6 except that 57 g of polyoxyethylene (12) tridecyl ether as non-ionic surfactant, is added after the Marlon AS3 abd the terminated dimethylpolysiloxane has a viscosity of approximately 60,000 mPa sec. (cP). This masterbatch emulsion had average mean particle size of 0.31 micron.

Reaction Conditions for Example 6 to 11

For the examples 6 to 11 presented in the summary table, between 450 and 900 g of masterbatch emulsion described above were poured was poured in a 1 liter double-wall glass reactor. The temperature was decreased until the "starting temperature" and, in order to start the emulsion polymerisation reaction, a certain quantity of sulphuric acid 10% to reach the right R+ was added under stirring (500 rpm) for 5 minutes. After 5 minutes, the stirring rate was decreased to 250 rpm. The temperature of the reaction was decreased slowly down to the "final temperature" in 4 hours. The reaction was stopped by the addition of enough triethanolamine to reach a pH between 7 and 7.5 once the desired final viscosity is reached.

Example 6a, b and c show that a large range of R+ can be used. Still the formation of cyclics is low and the final viscosity is reasonably high without impairing strongly the reaction rate Examples 7a and 7b show the influence of the benefit of using a temperature ramp during the reaction compared to a constant temperature. Example 7a is carried out at 10° C. and the polymerization of the example 7b is started at 21° C. and then the temperature decreased down to 10° C. after 4 hours of reaction. One can see that after 5 hours of reaction, a higher internal phase viscosity is obtained in the case of use of the temperature ramp profile instead of a constant temperature, keeping below 0.1% the formation of D4 and D5.

Example 8 shows the same thing despite the use of a less viscous hydroxyl-terminated organopolysiloxane at the starting point. After 7.5 hours of reaction, the final viscosity is obtained keeping below 0.1% the formation of D4 and D5.

In addition to a reduction of the reaction, the advantageous of starting at 20° C. instead of 10° C. is a reduction of the total production batch time. Indeed, few hours are required to cool down the full reactor to 10° C.

Example 9 shows that high final viscosity and low formation of D4 and D5% is obtained with another ramp of temperature with a starting temperature of 18° C. reduced to 15° C. after 4 hours.

Example 10 needs to be compared to Example 7a. The addition of a non-ionic surfactant in example 10 allows reducing particle size from 0.4 to 0.3 um. The polymerization was carried out as for the other examples. Despite the presence of the non-ionic surfactant, a final viscosity of 1110 Pa·s is reached in 10 hours still with a formation of cyclics inferior to 0.1%.

Example 11

Triethanolamine, Marlon AS 3 (alkylbenzene sulfonic acid), Me$_2$SiOH terminated dimethylpolysiloxane having a viscosity of approximately 20,000 mPa sec. (cP) and water were feed to a premix mixer running at 500 rpm and then to a high shear dynamic mixer (Homomic Line Mill) running at 3000 rpm. The detailed process is described in the example 1 and 2 of the patent EP 1352011. The rate of feeding of Triethanolamine, Marlon AS 3 (alkylbenzene sulfonic acid), Me$_2$SiOH terminated dimethylpolysiloxane and water was respectively 15 kg/h, 16.5 kg/h, 325 kg/h and 7 kg/h which gives a composition respectively of 4.2 wt %, 4.5 wt %, 89.4 wt %, 1.9 wt %.

Thus the various non-limiting examples show a small level of cyclics production compared with the comparative example outwith the scope of the invention.

Embodiments of the invention may be used in a variety of applications such as hair shampoos, hair conditioners, leather treatment or for a delivery formulation for skin care products. They may also be used in paper or textile coating and home care applications.

Improvements and modifications may be made without departing from the scope of the invention.

The invention claimed is:

1. A method of preparing an emulsion containing particles of an organopolysiloxane polymer having an average particle diameter of less than 1 μm, the method comprising:
   (i) combining a silanol end-blocked organosiloxane starting polymer, water, and a surfactant, wherein said starting polymer has a viscosity of at least 2 Pa·s and up to 150 Pa·s;
   (ii) emulsifying the starting polymer by agitating or shearing the starting polymer, water and surfactant;
   (iii) polymerizing the starting polymer to form a longer chain silanol end-blocked organopolysiloxane polymer; wherein at least a portion of said polymerizing step is performed at a temperature of less than or equal to 16° C., and wherein the emulsion contains less than 0.1 wt % of octamethylcyclotetrasiloxane and less than 0.1 wt % decamethylcyclopentasiloxane.

2. The method as claimed in claim 1, wherein the viscosity of the starting polymer is up to 100 Pa·s.

3. The method as claimed in claim 1, wherein the surfactant is an anionic surfactant.

4. The method as claimed in claim 1, wherein the polymerizing step is started at a temperature of at least 18° C. and then lowered to said temperature of less than or equal to 16° C.

5. The method as claimed in claim 1, wherein the portion of the polymerizing step performed at the temperature of less than or equal to 16° C. is also performed at a temperature more than 2° C.

6. The method as claimed in claim 1, wherein the portion of the polymerizing step performed at less than or equal to 16° C. is at least 30% of the total polymerization time.

7. The method as claimed in claim 1, wherein the polymerizing step takes place for 1 to 24 hours.

8. The method as claimed in claim 1, wherein the average particle diameter is less than 0.8 μm.

9. The method as claimed in claim 1, wherein the method is a continuous process and the starting polymer, surfactant and water are continuously fed to a high shear mixer in such proportions so as to form a viscous oil in water emulsion which is continuously withdrawn from the mixer.

10. The method as claimed in claim 1, wherein the starting polymer, surfactant and water are fed into a high shear mixer through a single supply line and the pressure in the supply line at the inlet to the high shear mixer is monitored to be within 20% of a target pressure predetermined to give a desired emulsion particle size.

11. The method as claimed in claim 10 wherein the target pressure is within the range of 0.05 to 40 bar.

12. The method as claimed in claim 1, wherein the surfactant is anionic and comprises a base.

13. The method as claimed in claim 12, wherein the polymerizing step includes combining a condensation catalyst with the starting polymer and wherein the amount of condensation catalyst is calculated as R+ being between 0.1 and 5, wherein R+ is defined as the ratio between the molar amount of catalytically active anionic surfactant plus the molar amount of condensation catalyst, minus the molar amount of base, all divided by the molar amount of catalytically active anionic surfactant.

14. The method as claimed in claim 1, wherein the starting polymer has a formula

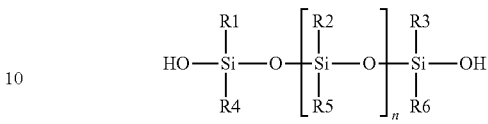

wherein $R_1$ to $R_6$ represent an alkyl group containing 1-6 carbon atoms or an aryl group, and n is in the range of 300-2000.

15. The method as claimed in claim 14, wherein n is in the range of 500-2000.

16. The method as claimed in claim 1, wherein the viscosity of the polymerized particles after the polymerizing step is from 600 Pa·s to 5000 Pa·s.

17. A composition comprising the emulsion prepared according claim 1.

18. The composition as claimed in claim 17, the composition being suitable within a hair shampoo, hair conditioner, hair treatment, for skin care products, leather treatment, for paper or textile treatment or home care applications.

19. The method as claimed in claim 1, wherein the surfactant is an anionic surfactant with one or more non-ionic surfactants.

20. A composition comprising an emulsion containing particles of a silanol end-blocked organopolysiloxane polymer having an average particle diameter of less than 1 μm, the composition containing less than 0.1 wt % of octamethylcyclotetrasiloxane and less than 0.1 wt % decamethylcyclopentasiloxane, and wherein the emulsion has an internal phase viscosity from 600 Pa·s to 5000 Pa·s.

21. The composition as claimed in claim 20, the composition being suitable within a hair shampoo, hair conditioner, hair treatment, for skin care products, leather treatment, for paper or textile treatment or home care applications.

* * * * *